(12) United States Patent
Hamann et al.

(10) Patent No.: US 9,334,431 B2
(45) Date of Patent: May 10, 2016

(54) HOT MELT ADHESIVE BASED ON LOW MELTING POINT POLYPROPYLENE HOMOPOLYMERS

(71) Applicant: Bostik, Inc., Wauwatosa, WI (US)

(72) Inventors: Richard Hamann, New Berlin, WI (US); Lianne Rachow, Milwaukee, WI (US)

(73) Assignee: BOSTIK, INC., Wauwatosa, WI (US)

( * ) Notice: Subject to any disclaimer, the term of this patent is extended or adjusted under 35 U.S.C. 154(b) by 0 days.

(21) Appl. No.: 14/284,381

(22) Filed: May 21, 2014

(65) Prior Publication Data

US 2014/0350155 A1    Nov. 27, 2014

Related U.S. Application Data

(60) Provisional application No. 61/855,775, filed on May 23, 2013.

(51) Int. Cl.
*C09J 157/02*    (2006.01)
*C09J 123/12*    (2006.01)
*C08L 91/06*    (2006.01)

(52) U.S. Cl.
CPC .............. *C09J 157/02* (2013.01); *C09J 123/12* (2013.01)

(58) Field of Classification Search
CPC ..... C09J 157/02; C09J 123/12; C08L 23/142; C08L 91/06
USPC .......................................... 524/226, 528, 369
See application file for complete search history.

(56) References Cited

U.S. PATENT DOCUMENTS

| 6,797,774 | B2 | 9/2004 | Kijima |
| 7,776,242 | B2 | 8/2010 | Sato et al. |
| 2005/0159566 | A1 | 7/2005 | Minami et al. |
| 2006/0093764 | A1 * | 5/2006 | Mehta ..................... B65B 63/08 428/35.2 |
| 2014/0147669 | A1 | 5/2014 | Thatcher et al. |
| 2014/0199545 | A1 | 7/2014 | Moriguchi et al. |
| 2014/0199907 | A1 | 7/2014 | Moriguchi et al. |

FOREIGN PATENT DOCUMENTS

| EP | 1498432 A1 * | 1/2005 | .............. C08F 10/06 |
| WO | WO 2013039261 A1 * | 3/2013 | .............. C09J 123/12 |
| WO | WO 2013039262 A1 * | 3/2013 | .............. C09J 123/12 |

OTHER PUBLICATIONS

PCT Search Report mailed Jul. 30, 2014 for corresponding PCT International Application No. PCT/US2014/039041.
PCT Written Opinion mailed Jul. 30, 2014 for corresponding PCT International Application No. PCT/US2014/039041.

* cited by examiner

*Primary Examiner* — Michael M Bernshteyn
(74) *Attorney, Agent, or Firm* — Wozney Law, LLC; Thomas M. Wozny

(57) ABSTRACT

A hot melt adhesive for use on porous substrates, wherein the hot melt adhesive has
  a) about 10% to about 70% by weight of a polypropylene homopolymer having a DSC melting point of less than 100° C.;
  b) about 10% to about 60% of a first tackifying resin having a Ring & Ball Softening Point of about 95° C. to about 140° C.;
  c) about 0% to about 65% of a second tackifying resin that is different than the first tackifying resin;
  d) about 5% to about 50% of a plasticizer;
  e) about 1% to about 40% by weight of a secondary polymer which is either a semi-crystalline polymer or wax with an enthalpy of fusion of greater than 30 Joules/gram;
  f) about 0.1% to about 5% of a stabilizer or antioxidant;
wherein the components total 100% by weight of the composition, and the viscosity of the composition is equal to or less than about 20,000 centipoise (cP) at 163° C. (325° F.).

26 Claims, No Drawings

HOT MELT ADHESIVE BASED ON LOW MELTING POINT POLYPROPYLENE HOMOPOLYMERS

BACKGROUND OF THE INVENTION

The present invention relates to hot melt adhesives, and more particularly to a hot melt adhesive using low molecular weight, low modulus polypropylene polymers. This adhesive gives high initial bond strength in spite of the long crystallization time of the polypropylene polymer. Additives are used in combination with the polypropylene polymer to increase the adhesive's crystallization time and setting speed. This is necessary for applications where high green strength or low bleed-through is required.

Hot melt adhesives are used to bond a wide variety of substrates together in a range of industrial processes. Some of these end uses include sealing cartons and corrugated boxes, labels for a wide variety of applications, and assembling disposable diapers. For some applications the hot melt is a fairly hard, flexible solid material with no surface tack immediately after adhesive application. One example would be for a carton sealing application where the product needs to "set up" or solidify quickly to hold the carton flaps in place seconds after the hot melt application. For other applications, the hot melt needs to have appreciable surface tack after it cools, for example when used as a pressure sensitive tape or label where the adhesive must bond to another substrate at room temperature.

For some other applications such as diaper construction, the adhesive is applied to the substrate in a molten state but must immediately build strength so that it will hold the article together even though there are forces acting on the adhesive bond. One common end use for hot melts is to bond the elastic strands in a diaper in place. The adhesive must be able to resist the contractive force of the elastic strands, since the elastic strands are elongated before they are bonded into the diaper. One other challenge is to ensure that the adhesive does not bleed-though the substrates it is in contact with. Nonwoven fabrics are frequently used in the production of disposable articles and care must be used so that the adhesive does not bleed-through the nonwoven. If this occurs, it can build on rollers or compressions sections of the diaper line. Many of the adhesives used to make disposable articles are pressure sensitive in nature since this tends to give the hot melt a wider process window. So a balance must be achieved between a relatively low viscosity for ease of application, fast development of internal strength to hold the substrates together immediately after being applied and resistance to bleed-through even if the adhesive is soft and/or pressure sensitive.

Typically hot melt adhesives can be based on polymers such as polyolefins (e.g. ethylene or propylene based polymers), or functionalized polyolefins (ethylene or propylene copolymers with oxygen containing monomers), or styrenic block copolymers containing at least one rubbery phase, like styrene-isoprene-styrene (SIS), or styrene-butadiene-styrene (SBS) polymers. Styrenic block copolymers are commonly used for diaper construction applications where nonwoven fabrics are frequently used. They tend to be very resistant to bleed-through on these materials. It is thought this is due to the speed at which the styrene endblocks reform after application, which happens very quickly as the hot melt cools. Hot melts that are not based on styrenic block copolymers must cool and re-crystallize after application to some degree to resist bleed-though.

Over the years, many different olefinic polymers have been used in the formulation of hot melt adhesives used in the construction of disposable soft goods. One type is amorphous polyalpha olefins, also known as APAO. They were primarily produced using Ziegler-Natta catalysis and could be made using a variety of monomers, including but not limited to propylene, ethylene and butene. Many different types of APAO copolymers and terpolymers are produced by a number of manufacturers. They include Evonik Industries, who produce the Vestoplast® polymers; REXtac, LLC, who produces the Rextac® RT range of materials and Eastman Chemical, manufacturers of the Eastoflex® line of polymers. They are all characterized by having a very low degree of crystallinity as measured by DSC. As commercially produced, they are random polymers having broad molecular weight distributions.

When formulated into hot melt adhesives for the construction of disposable articles, APAO's had some deficiencies due to their amorphous character. While they are useful for diaper construction applications (bonding the nonwoven to the polyethylene) they did not possess the level of elevated temperature creep resistance needed for the elastic attachment application. Another deficiency is that they tend not to spray well using conventional hot melt application equipment.

Older Ziegler-Natta catalyzed polyolefins such as polyethylene or polypropylene have not been used widely for diaper construction applications. While these polymers are used in hot melt adhesives for packaging applications (e.g. case and carton sealing), they lack the adhesion, open time and sprayability needed for disposable article construction applications. Examples of these types of polymers include the Epolene® polymers from Westlake Chemical Company, although many other manufacturers product these types of polyolefin polymers.

These older types of Ziegler-Natta catalyzed polyolefin polymers typically have very high melting points because of their high level of crystallinity. This gives a hot melt that has a very high melting point which in turn means the adhesive needs to be applied at very high temperatures, for example higher than 160° C. or even 170° C. This is undesirable since many of the substrates used in the nonwoven industry are very thin and are very sensitive to high temperatures.

More recently, polyolefins have been made using metallocene catalysis instead of the older Ziegler-Natta catalysis. Some of these new polymers have found use in the development of hot melt adhesives. However, they have not found widespread use in the manufacture of disposable articles since they tend not to spray well, their temperature application window is narrow and their adhesion to certain substrates has been poor.

The standard in the disposable industry in terms of sprayability have been hot melts based on styrenic block copolymers, particularly styrene-isoprene-styrene (SIS) block copolymers. No olefinic based polymer has been able to match the characteristics of the styrenic block copolymers in terms of ease of sprayability, performance and temperature application window.

In recent years, there has been significant changes in the way that energy has been produced, particularly in the United States. There has been tremendous increases in the amount of natural gas that is produced because of the rise of "hydraulic fracturing" or "fracking" When natural gas is processed, there is a much higher ratio of low molecular weight constituents ($C_2$, $C_3$, and $C_4$) produced versus higher molecular weight materials ($C_5$ and higher). This translates into better availability and lower cost for olefins like polyethylene and polypropylene versus other materials where $C_5$ through $C_9$ monomers are required (e.g. isoprene, styrene and other aromatic monomers).

Therefore, a need exists to have a hot melt adhesive that is based on olefins, such as ethylene and propylene, to take advantage of the increased availability of natural gas and other lower molecular weight cracking feeds, but that has better performance and application characteristics than currently available polyolefin polymers.

SUMMARY OF THE INVENTION

A new type of polyolefin polymer has been developed by Idemitsu Petrochemical, Ltd. They are described as their L-MODU grades, which is short for Low Molecular Weight and Low Modulus Polyolefin. Although they are entirely polypropylene based, they have properties not normally associated with polypropylene polymers. Conventional polypropylene homopolymers tend to be very high in crystallinity and melting point. This is true whether or not they were prepared using Zeigler-Natta or metallocene catalyst technology. The new L-MODU grades are made using a unique metallocene catalyst which controls the stereoregularity of the polymer. This results in a new type of polymer which gives properties that were not attainable before.

The present invention uses Idemitsu's new L-MODU polymers as the base polymer(s) in the formulated hot melt adhesive. The L-MODU polymer is used at a level of about 10 percent to about 70 percent by weight. A tackifying resin is also a critical part of the formulation and is present from about 10 percent to about 60 percent by weight. Another critical component is a plasticizer which is used from about 5 percent to about 50 percent by weight. The fourth important component is from about 1 percent to about 40 percent by weight of a secondary additive, such as a wax or semi-crystalline polymer which is used to increase the setting speed of the adhesive. Without this component, the open time of the adhesive is too long, which causes a weak bond to form initially and can also cause bleed-through if the adhesive is used on a porous substrate, such as a nonwoven fabric.

The present invention solves the important problem of having a sprayable, olefinic-based hot melt adhesive using the same application parameters as those currently used, such as coating techniques and add-on levels while providing the same level of performance expected with current SIS and SBS based technologies, (i.e. high bond strength levels, creep resistance, peel force and heat resistance). When formulated into a hot melt adhesive, these polypropylene polymers offer improved spray characteristics compared to APAO based hot melt adhesives or those based on the older Ziegler-Natta or metallocene catalyzed generations of polyolefins. In particular, when formulated in combination with a semi-crystalline material, such as a semi-crystalline polymer or wax, a hot melt adhesive can be produced with a unique combination of adhesion, elevated temperature resistance, sprayability and resistance to bleed-through on porous substrates. This combination of properties has not previously been achieved in a hot melt without using a styrenic block copolymer as the base polymer. In addition, compared to conventional SIS based or SBS based adhesives, the L-MODU polymers offer improved viscosity stability when stored at elevated temperatures for prolonged periods of time (e.g. 48 hours at 177° C.).

DETAILED DESCRIPTION OF THE INVENTION

A new type of polyolefin has been developed by Idemitsu Petrochemical, Ltd. They have been described as their L-MODU grades, which is short for Low Molecular Weight and Low Modulus Polyolefin. Although they are entirely polypropylene based, they have properties not normally associated with polypropylene. Conventional polypropylene homopolymers tend to be very high in crystallinity and melting point. This is true whether or not they were prepared using Zeigler-Natta or metallocene catalysts technology. The new L-MODU grades are made using a unique metallocene catalyst which controls the stereoregularity of the polymer. This results in a new type of polymer which gives properties that were not attainable before. For example, the melting points of these new polymers are much lower than any other metallocene catalyzed polypropylene homopolymer. Typical polypropylene homopolymers have Melt Peaks of about 130° C. to 170° C. when measured by Differential Scanning calorimetry as in ASTM E794-01. The new L-MODU polymers have Ring and Ball Softening points of under 130° C. when measured according to ASTM E-28-99. When measured using Differential Scanning calorimetry (DSC) according to ASTM E-794-01, they have melting points less than 100° C. and more preferably between 60° C. and 90° C.

The process to make these polymers is described in detail in U.S. Pat. No. 6,797,774 (assigned to Idemisui Petrochemical Co., Ltd. of Tokyo, JP) along with various hot melt adhesive formulations. Because they have such low melting points and long recrystallization times, special considerations need to be taken into account to process them using underwater pelletizing equipment. This is described in U.S. Pat. No. 7,776,242 assigned to Idemitsui Kosan Co, Ltd. of Tokyo, JP. The disclosures found in U.S. Pat. No. 6,797,774 and U.S. Pat. No. 7,776,242 are both specifically incorporated into the present patent application by reference thereto.

However, we have found that when the Idemitsu L-MODU polymers are used as the sole polymer in the hot melt formulation, as they are in the prior art reference U.S. Pat. No. 6,797,774 noted above, the setting speed is much too slow and there is a high tendency for bleed-through. We have found that this can be remedied by adding a secondary additive, such as a wax or semi-crystalline polymer to increase the set speed and minimize or eliminate bleed-through. The secondary additive can simply recrystallize on its own to stop the bleed-through or it can nucleate the L-MODU polymer to cause it to crystallize faster. It may also bloom to the surface to prevent sticking to the substrate.

Even though the L-MODU polymers are polypropylene homopolymers, they are very different from traditional polypropylene polymers, as mentioned previously. Besides having much lower melting points when measured by DSC, their Melt Enthalpy values are also much lower than traditional polypropylene grades. When analyzed according to ASTM E793-01 "Standard Test Method for Enthalpies of Fusion and Crystallization by Differential Scanning Calorimetry", the following results are obtained. The test was modified slightly to use a scanning temperature of 20° C. per minute instead of 10° C. per minute.

| L-MODU grade | Glass Transition Temperature (Tg) | Melt Peak | Melt Enthalpy |
|---|---|---|---|
| S-400 | −9.7° C. | 77.6° C. | 4.9 Joules/gram |
| S-600 | −7.8° C. | 77.1° C. | 22.6 Joules/gram |
| S-901 | −8.0° C. | 76.9° C. | 22.6 Joules/gram |

Both the Melt Peak and Melt Enthalpy values are very low compared to most traditional polypropylene based homopolymers. Typical polypropylene homopolymers have melting points of from about 130° C. to 171° C. and melt enthalpy values of about 80 J/g or higher. The L-MODU polymers have a unique combination of melting point and melt enthalpy. However, to make a suitable hot melt adhesive using these materials as a base polymer requires the use of an additional semi-crystalline polymer as a secondary additive.

The reason that bleed-through is such a significant issue is that it can cause significant downtime on the equipment, defective product, increased scrap level as well as consumer complaints. If the bleed-through causes build up on the equipment, on rollers for example, it can cause substrates to stick to the rollers which can result in tearing of the substrates or the finished goods. This can cause increased scrap rates as well as downtime of the equipment when the production line needs to be stopped for cleaning. When the equipment runs at a thousand feet per minute and produces hundreds of finished articles per minute, any downtime is very expensive. If the adhesive builds up and gets transferred to the finished article and winds up in the consumer package, this can also cause customer complaints as well.

A wide variety of waxes and other semi-crystalline polymers can be used as the secondary additive to provide this function. Typical waxes such as paraffin wax, microcrystalline wax, Fischer-Tropsch wax, or polyethylene or polypropylene waxes can all be used. Polyolefin polymers can also be used to provide this function. They are produced in a wide range of molecular weights, monomers, densities and crystallinity levels. They are also made using an ever widening range of catalysts, including Ziegler-Natta catalysts, metallocene and other single site catalysts.

Polymers in general can range in crystallinity from very low, such as with amorphous polypropylene or amorphous poly-alpha-olefins to those that are very high, such as isotactic polypropylene. The crystallinity of a polymer can be determined by Differential Scanning calorimetry (DSC) or X-ray Diffraction techniques. DSC is the most widely used technique in the adhesive industry. The Enthalpy of Fusion (also known as latent heat of melting or heat of fusion) can be measured and quantified using ASTM E793-01 entitled "Standard Test Method of Enthalpies of Fusion and Crystallization by Differential Scanning calorimetry". The enthalpy of fusion is the amount of energy it takes to melt the crystalline portion of the polymer. This value is generally reported in Joules/gram (J/g).

This number varies widely from almost zero to upwards of 250 Joules/gram depending on the crystallinity of the polymer. Theoretically, a truly amorphous polymer would have no crystallinity, no melting point and therefore an enthalpy of fusion of zero. As it states in U.S. Pat. No. 7,524,911 granted to Dow Global Technologies (column 8, lines 30-33), "The term 'amorphous' refers to a polymer lacking a crystalline melting point as determined by differential scanning calorimetry (DSC) or equivalent technique".

As a practical matter, most polymers that are sold as "amorphous poly-alpha-olefins" (APAO) have some low level of crystallinity. On the other hand, polymers that are considered crystalline are not 100 percent crystalline. In Dow's '911 patent it states at column 8, lines 26-30, "The term 'crystalline' refers to a polymer that possesses a first order transition or crystalline melting point (Tm) as determined by differential scanning calorimetry (DSC) or equivalent technique, and this term may be used interchangeably with the term 'semi-crystalline'."

It is useful to have some quantifiable boundary between a polymer that is considered an "amorphous" polymer and those considered "semi-crystalline" or "crystalline". U.S. Pat. No. 6,747,114 (granted to ExxonMobil Chemical Patents Inc. of Houston, Tex.) states at column 8, lines 9-14, "The semi-crystalline polymer preferably has a heat of fusion from about 30 J/g to about 80 J/g as determined by DSC, more preferably from about 40 J/g to about 70 J/g as determined by DSC, and most preferable from about 50 J/g to about 65 J/g as determined by DSC."

Bostik's own internal analysis correlates with the descriptions above. The "amorphous poly-alpha olefins" are not in fact entirely amorphous but possess a very low level of crystallinity as measured by DSC. The analysis of many of the grades sold by Eastman Chemical Co. as "Amorphous Polyolefins" under the trade name Eastoflex® and those sold by Evonik Industries as "Amorphous Poly-alpha-olefins" under the trade name Vestoplast® and those manufactured by REXtac, LLC. as REXtac® RT show that all of them have an enthalpy (or heat) of fusion of less than 25 Joules/gram. The single highest value obtained was 20.4 Joules/gram for Vestoplast® 708. One of the two grades shown in U.S. Pat. No. 7,517,579 (assigned to Kimberly-Clark Worldwide, Inc.) is RT2730, which has a heat of fusion of 9.4 Joules/gram. The other grade that is mentioned is RT2723, which according to REXtac's usual nomenclature should be a lower viscosity version of RT2730 with the same monomer ratios. Therefore, the enthalpy of fusion should be similar to RT2730. In summary, currently available data strongly indicates that any grade of polymer currently sold as an "amorphous poly-alpha-olefin" would have an enthalpy of fusion value of less than about 25 Joules/gram.

A wide range of other polyolefins are produced by a variety of manufacturers that fall under the category of "semi-crystalline" polymers. They have heat of fusion values of greater than about 30 Joules/gram, which puts them outside the range of APAO's. For example, ethylene vinyl acetate copolymers range from about 35 Joules/gram for a high vinyl acetate grade (40% vinyl acetate) to about 73 Joules/gram for a lower vinyl acetate grade (18% vinyl acetate). Polyalphaolefins such as Dow's Affinity® grades (metallocene catalyzed ethylene/octene copolymers) range from about 52 Joules/gram for Affinity® 8200, a relatively low density grade (0.870 g/cc, MI=5) to 77 J/g for a higher density grade (0.900 g/cc, MI=6) called Affinity® PL 1280. Dow also manufacturers a high melt index grade (0.870 g/cc, MI=1000) called GA1900 specifically for hot melt adhesives that has a heat of fusion of 57 Joules/gram. Clearly, these Affinity® polymers could not be considered to be amorphous and are not amorphous poly-alpha-olefins.

A more recent development in the area of polyolefins is what are referred to as "olefin block copolymers" or OBC. This is an entirely new class of polyolefin polymer produced using a chain shuttling catalysis technology that produces a linear block structure of the monomers rather than a random polymer produced by Ziegler-Natta or traditional metallocene technology. At this time, they are manufactured by Dow Chemical under the trade name of Infuse®. The OBC's consist of crystallizable ethylene-octene blocks (hard) with very low comonomer content and high melting temperature alternating with amorphous ethylene-octene blocks (soft) with high comonomer content and low glass transition temperature. This gives the polymer much better elevated temperature resistance and elasticity compared to a typical metallocene random polymer of similar density. While some of the grades of Infuse® have low heat of fusion (approximately 20 Joules/gram) they could not be considered to be amorphous poly-alpha-olefins because the polymer architecture is completely different (i.e. block vs. random) and is specifically produced to have crystalline regions.

For the purposes of this invention, the L-MODU polypropylene homopolymer is blended with a secondary additive, such as a wax, or other semi-crystalline polymer, that has a heat of fusion of greater than 30 joules per gram when measured using ASTM procedure E793-01. Additives that have greater than 30 J/g provide the finished adhesive with a sufficiently short open time to minimize bleed-through while also increasing the setting speed and heat resistance.

Accordingly, the present invention provides a hot melt adhesive composition, comprising a blend of the following components:

- about 10% to about 70%, preferably about 15% to about 60%, and most preferably about 20% to about 50%, by weight, of a polypropylene homopolymer having a DSC melting point of less than 100° C.;
- about 10% to about 60%, preferably about 15% to about 55%, and most preferably about 20% to about 50%, by weight, of a first tackifying resin having a softening point of at least about 95° C. and preferably a softening point of from about 95° C. to about 140° C.;
- about 0% to about 65% of a second tackifying resin that is different than the first tackifying resin;
- about 5% to about 50%, preferably about 10% to about 45%, more preferably about 15% to about 40%, by weight, of a plasticizer;
- about 0.1% to about 5% of a stabilizer or antioxidant; and
- about 1% to about 40%, preferably about 2% to about 35%, and more preferably about 2% to about 30%, by weight of a secondary additive different from the polypropylene homopolymer, the first and second tackifying resins and the plasticizer, said secondary additive being a semi-crystalline material with an enthalpy of fusion of greater than 30 Joules/gram, wherein the components total 100% by weight of the composition, and the viscosity (measured by ASTM D3236-88) of the composition is equal to or less than about 20,000 centipoise (cP) at 163° C. (325° F.), preferably equal to or less than 15,000 cP at 163° C., and more preferably equal to or less than 12,000 cP at 163° C.

The hot melt adhesive compositions of the present invention also comprises a solid tackifier which is compatible with the low melting point polypropylene homopolymer. Representative resins include the $C_5/C_9$ hydrocarbon resins, synthetic polyterpenes, rosin, rosin esters, natural terpenes, and the like. More particularly, the useful tackifying resins include any compatible resins or mixtures thereof such as (1) natural and modified rosins including gum rosin, wood rosin, tall oil rosin, distilled rosin, hydrogenated rosin, dimerized rosin, and polymerized rosin; (2) glycerol and pentaerythritol esters of natural and modified rosins, including the glycerol ester of pale, wood rosin, the glycerol ester of hydrogenated rosin, the glycerol ester of polymerized rosin, the pentaerythritol ester of hydrogenated rosin, and the phenolic-modified pentaerythritol ester of rosin; (3) copolymers and terpolymers of natural terpenes, such as styrene/terpene and alpha methyl styrene/terpene; (4) polyterpene resins generally resulting from the polymerization of terepene hydrocarbons, such as the bicyclic monoterpene known as pinene, in the presence of Friedel-Crafts catalysts at moderately low temperatures; also included are the hydrogenated polyterpene resins; (5) phenolic modified terpene resins and hydrogenated derivatives thereof such, for example, as the resin product resulting from the condensation, in an acidic medium, of a bicyclic terpene and a phenol; (6) aliphatic petroleum hydrocarbon resins resulting from the polymerization of monomers consisting primarily of olefins and diolefins; also included are the hydrogenated aliphatic petroleum hydrocarbon resins; and (7) cyclic petroleum hydrocarbon resins and the hydrogenated derivatives thereof. Mixtures of two or more of the above described tackifying resins may be required for some formulations. Also included are the cyclic or acyclic $C_5$ resins and aromatic modified acyclic or cyclic resins.

The tackifying resin should have a Ring and Ball softening point (measured by ASTM E28) of at least about 95° C., and preferably between about 95° C. and about 140° C., and most preferably the softening point is between about 95° C. and about 130° C. A preferred tackifier is a hydrogenated aromatic modified dicyclopentadiene resin with a Ring and Ball softening point between about 95° C. to 130° C. The most preferred tackifying resins are fully hydrogenated resins regardless of type like aliphatic or cycloaliphatic hydrocarbon resins such as, Eastotac® H100W, or Sukorez® SU210, a pure aromatic monomer resin such as Regalrez 1094, and DCPD (dicyclopentadiene) resins with no aromatic content such as Escorez 5400.

Also, other preferred tackifying resins are partially hydrogenated aliphatic hydrocarbon resins such as Eastotac H100L and Eastotac H100R, as well as non-hydrogenated aliphatic C5 resins and aromatic modified C5 resins with low aromaticity such as Piccotac 1095 and Piccotac 9095, respectively.

Tackifying resins may be present in amounts of about 10 to 60% by weight of the composition, preferably about 15 to 55% by weight are utilized, and most preferably about 20 to 50% by weight. Blends of two or more tackifying resins may also be used. For example, a blend of a first tackifying resin and a second tackifying resin that is different than the first tackifying resin may also be employed. From about 0% to about 65% by weight of one or more additional tackifying resins may be blended together with the first tackifying resin if desired.

Hot melt adhesive formulas according to the present invention also contain about 5% to about 50%, preferably about 10 to about 50%, and more preferably about 15% to about 40%, by weight, of a plasticizer. A suitable plasticizer may be selected from the group which not only includes the usual plasticizing oils, such as mineral oil, but also olefin oligomers and low molecular weight polymers, glycol benzoates, as well as vegetable and animal oil and derivatives of such oils. The petroleum-derived oils that may be employed are relatively high boiling temperature materials containing only a minor proportion of aromatic hydrocarbons. In this regard, the aromatic hydrocarbons should preferably be less than 30%, and more particularly less than 15%, by weight, of the oil. Alternately, the oil may be totally non-aromatic. The oligomers may be polypropylenes, polybutenes, hydrogenated polyisoprene, hydrogenated butadiene, or the like having average molecular weights between about 100 and about 10,000 g/mol. Suitable vegetable and animal oils include glycerol esters of the usual fatty acids and polymerization products thereof. Other plasticizers may be used provided they have suitable compatibility. Nyflex 222B, a naphthenic mineral oil manufactured by Nynas Corporation, has also been found to be an appropriate plasticizer. As will be appreciated, plasticizers have typically been employed to lower the viscosity of the overall adhesive composition without substantially decreasing the adhesive strength and/or the service temperature of the adhesive. The choice of plasticizer can be useful in formulation for specific end uses (such as wet strength core applications). Because of economics involved in production and in material cost, as plasticizers are usually of lower cost than other materials involved in the formulation like polymers and tackifying resins, the amount of plasticizer in the adhesive should be maximized for cost considerations.

The adhesive also typically includes about 0.1% to about 5% of a stabilizer or antioxidant. The stabilizers which are useful in the hot melt adhesive compositions of the present invention are incorporated to help protect the polymers noted above, and thereby the total adhesive system, from the effects of thermal and oxidative degradation which normally occurs during the manufacture and application of the adhesive as well as in the ordinary exposure of the final product to the ambient environment. Such degradation is usually manifested by a deterioration in the appearance, physical properties and performance characteristics of the adhesive. A particularly preferred antioxidant is Irganox 1010, a tetrakis (methylene(3,5-di-tert-butyl-4-hydroxyhydrocinnamate)) methane manufactured by Ciba-Geigy. Among the applicable stabilizers are high molecular weight hindered phenols and multifunctional phenols, such as sulfur and phosphorus-containing phenols. Hindered phenols are well known to those skilled in the art and may be characterized as phenolic compounds which also contain sterically bulky radicals in close proximity to the phenolic hydroxyl group thereof. In particular, tertiary butyl groups generally are substituted onto the benzene ring in at least one of the ortho positions relative to the phenolic hydroxyl group. The presence of these sterically bulky substituted radicals in the vicinity of the hydroxyl group serves to retard its stretching frequency and correspondingly, its reactivity; this steric hindrance thus providing the phenolic compound with its stabilizing properties. Representative hindered phenols include:

1,3,5-trimethyl-2,4,6-tris(3-5-di-tert-butyl-4-hydroxybenzyl)benzene;
pentaerythritoltetrakis-3(3,5-di-tert-butyl-4-hydroxyphenyl) propionate;
n-octadecyl-3(3,5-ditert-butyl-4-hydroxyphenyl)propionate;
4,4'-methylenebis(4-methyl-6-tert butylphenol);
4,4'-thiobis(6-tert-butyl-o-cresol);
2,6-di-tert-butylphenol;
6-(4-hydroxyphenoxy)-2,4-bis(n-ocytlthio)-1,3,5-triazine;
2,4,6-tris(4-hydroxy-3,5-di-tert-butyl-phenoxy)-1,3,5-triazine;
di-n-octadecyl-3,5-di-tert-butyl-4-hydroxybenzylphosphonate;
2-(n-octylthio)ethyl-3,5-di-tert-butyl-4-hydroxybenzoate; and sorbitol hexa-(3,3,5-di-tert-butyl-4-hydroxy-phenyl) propionate.

The performance of these stabilizers may be further enhanced by utilizing, in conjunction therewith synergists such as, for example, thiodipropionate esters and phosphites.

The adhesive composition useful in the method of the present invention may be produced using any of the techniques known in the art. A representative example of the procedure involves placing all of the substances, in a jacketed mixing kettle, and preferably in a jacketed heavy duty mixer of the Baker-Perkins or Day type, and which is equipped with rotors, and thereafter raising the temperature of this mixture to a range of 120° C. to 177° C. It should be understood that the precise temperature to be used in this step would depend on the melting point of the particular ingredients. The resulting adhesive composition is agitated until the polymers completely dissolve. A vacuum is then applied to remove any entrapped air.

Up to 25% of optional ingredients may be incorporated into the adhesive composition in order to modify particular physical properties. These ingredients may include colorants, such as titanium dioxide and fillers such as talc, calcium carbonate and clay, cross-linking agents, reactive compounds, fire-retardant mineral or organic agents, as well as ultraviolet light (UV) absorbing agents and UV fluorescing agents. These optional ingredients are well known in this art.

Polyolefin nucleating agents may also be also present in the invention. Nucleating agents speed the crystallization of a polyolefin by providing a site for the crystals to form. The result is that the polyolefin polymer not only recrystallizes faster, but also more completely, which results in the adhesive having a higher Ring and Ball softening point and better heat resistance. The nucleating agent appears to be more effective when there is a secondary semi-crystalline additive present than when it is absent. Nucleating agents suitable for this invention are generally of the sub class of nucleating agents known as clarifying agents that are commonly employed in polyolefins additive packages to promote rapid crystallization. Suitable materials include dibenzylidene sorbitol derivatives such as Millad 3988 and Millad NX8000 supplied by Milliken as well as Irgaclear D produced by BASF. Other suitable agents include aromatic amide systems such as NJ Star NU-100 provided by New Japan Chemical Company.

The nucleating agent is generally present in the adhesive compositions in amounts of about 0.05 to 5.0% by weight of the composition, preferably about 0.1 to 2.5% by weight are utilized, and most preferably about 0.2 to 1.0% by weight. Blends of two or more nucleating agent may also be used. For example, a blend of a nucleating agent and a second nucleating agent that is different than the first nucleating agent may also be employed. From about 0.05% to about 5.0% by weight of one or more additional nucleating agent may be blended together with the first nucleating agent if desired. The nucleating agent may be used directly as a powder, as a slurry in a portion of suitable plasticizing agent, or as a component in a masterbatch of a suitable polymer such as Milliken NX-10.

Various methods are conventionally used to coat a hot melt adhesive at fairly low viscosity on a substrate. This can be made by roll coating or any printing type method, or by slot coating, by extrusion or by spray gun. Spray gun techniques are numerous and can be done with or without assistance of compressed air that would shape the adhesive spray, and consequently the adhesive pattern. The hot melt adhesive material is generally allowed to melt in tanks, and then pumped through hoses to the final coating spot on the substrates.

EXAMPLES

Hot melt adhesive were prepared with the ingredients and mixing procedures described herein below. A total of 2000 grams each were made and the mixing was carried out at about 150° C. to 190° C. under carbon dioxide atmosphere in a laboratory type mixer that consists of a propeller powered by a motor, a heating mantle, a temperature control unit and a container of about 1 gallon in size. The appropriate amounts of each component, calculated according to the ratios shown in the tables below, were added to the container in an appropriate sequence to allow mixing while limiting the heat or shear degradation of ingredients. After the ingredients in the container were completely melted and mixed thoroughly to insure good homogeneity, samples were stored appropriately to be tested.

The base polymer was one of the Idemitsu L-MODU polypropylene homopolymers listed in Table One.

TABLE ONE

| Properties | L-MODU S400 | L-MODU S600 | L-MODU S901 |
|---|---|---|---|
| Density (kg/m$^3$) | 870 | 870 | 870 |
| DSC Softening point (° C.)# | 78 | 78 | 79 |
| Molecular weight (weight average) | 45,000 | 70,000 | 120,000 |
| Molecular weight distribution | 2 | 2 | 2 |

TABLE ONE-continued

| Properties | L-MODU S400 | L-MODU S600 | L-MODU S901 |
|---|---|---|---|
| Tensile modulus (MPa) | 60 | 60 | 60 |
| Elongation at break (%) | 600 | 800 | 900 |
| Brookfield Melt viscosity at 190° C. (cP) | 9,000 | 52,000 | * |

The DSC Softening points were run by Bostik's Analytical Laboratory. The other values were reported by Idemitsu on their web site.
* MFR = 50 g/10 min for 2.16 kg of L-MODU S901 at 230° C.

Formulations were prepared as listed in U.S. Pat. No. 6,797,774 as shown in Table 2. To best match the viscosity of the P1 polymer given in Table 1 of '774, it was determined that a blend of 1 part L-MODU 5600 to 4 parts L-MODU S 400 was required.

TABLE TWO (Prior Art)

| Raw Material | Ex. 1 of '774 | Ex. 1A | Ex. 2 of '774 | Ex. 2A | Ex. 3 of '774 | Ex. 3A |
|---|---|---|---|---|---|---|
| I-MARV P-125 | 40.0 | 40.0 | 30.0 | 30.0 | | |
| I-MARV P-90 | | | | | 40.0 | 40.0 |
| Escorez 5400 | | | | | | |
| P1 polymer from '774 | 60.0 | | 60.0 | | 60.0 | |
| L-MODU S901 | | | | | | |
| L-MODU S600 | | 12.0 | | 12.0 | | 12.0 |
| L-MODU S400 | | 48.0 | | 48.0 | | 48.0 |
| Paraffinic Process Oil | | | 10.0 | 10.0 | | |
| TOTAL | 100.0 | 100.0 | 100.0 | 100.0 | 100.0 | 100.0 |
| Melt Viscosity 180° C. (cP) | 7000 | 6360 | 4500 | 3910 | 6100 | 4850 |

The melt viscosity of Example 1, 2 & 3 are as shown in Table Two of U.S. Pat. No. 6,797,774.

TABLE THREE (Inventive)

| Raw Material | Ex. A | Ex. B | Ex. C | Ex. D | Ex. E | Ex. F |
|---|---|---|---|---|---|---|
| Escorez 5400 | 29.6 | 29.6 | 29.6 | 29.6 | 29.6 | 29.6 |
| L-MODU S901 | 10.9 | 10.9 | 10.9 | 10.9 | 5.9 | 10.9 |
| L-MODU S600 | 24.4 | 24.4 | 24.4 | 24.4 | 24.4 | 24.4 |
| Pro-fax RP501V | | | 2.0 | | | |
| Pro-fax RP591V | | | | | | 4.0 |
| Kraton G-1657 | | | | | 5.0 | |
| 104N wax | | 2.0 | | | | |
| A-C 1089 | | | | 2.0 | 2.0 | |
| 150 MP Paraffin wax | 8.0 | 6.0 | 6.0 | 6.0 | 6.0 | 4.0 |
| Process Oil PW-90 | 27.1 | 27.1 | 27.1 | 27.1 | 27.1 | 27.1 |
| TOTAL | 100.0 | 100.0 | 100.0 | 100.0 | 100.0 | 100.0 |
| Melt Viscosity at 177° C. (cP) | 2200 | 2900 | 3950 | 3150 | 2950 | 5350 |
| R&B Softening Point (° C.) | 72 | 94 | 122 | 93 | 91 | 124 |

Raw Materials Used in the Tables

I-MARV tackifying resins are fully hydrogenated hydrocarbon resins manufactured by Idemitsu Kosan Co., Ltd. The "P" indicates the product is fully hydrogenated and the number in the name is the resin's softening point in degrees Celsius.

Escorez 5400 is a fully hydrogenated hydrocarbon resin with a softening point of 100° C. It is manufactured by ExxonMobil Chemical Co.

Sukorez SU-210 is a hydrogenated C5/Cyclic hydrocarbon resins with a R&B Softening Point of 110° C. It is available from Kolon Industries of South Korea.

Piccotac 9095 is an aromatic modified C5 resin with a 94° C. R&B Softening Point. It is available from Eastman Chemical Co.

Eastotac H-100R is a hydrogenated hydrocarbon resin with a 100° C. R&B Softening Point and a molten Gardner Color of 4. It is available from Eastman Chemical Co.

P1 is the polymer as described in U.S. Pat. No. 6,797,774. Since Bostik could not polymerize that exact polymer, we used a blend of commercially available polymers of the same type from Idemitsu. The ratio of available grades was selected to duplicate the viscosity of the P1 polymer as closely as possible.

L-MODU grades were obtained from Idemitsu Co. of Japan. The physical properties of those grades are shown in Table One.

Pro-fax RP501V is a high flow, propylene impact copolymer that contains isotactic polypropylene and an ethylene-propylene rubber phase. It is produced by LyondellBasell Polymers. It has a melt flow of 100 g/10 minutes when measured according to ASTM D-1238 using a 2.16 kilogram weight and a test temperature of 230° C. The density of this polymer is 0.90 grams/cc. It has a Melt Peak of 163° C. and a Melt Enthalpy of 81.1 Joules/gram when measured by Differential Scanning calorimetry. The test procedures used are ASTM E793-01 and ASTM E794-01 respectively.

Pro-fax RP591V is a high flow, random polypropylene copolymer produced by LyondellBasell Polymers. It has a melt flow of 100 g/10 minutes when measured according to ASTM D-1238 using a 2.16 kilogram weight and a test temperature of 230° C. The density of this polymer is 0.90 grams/cc. It has a Melt Peak of 142° C. and a Melt Enthalpy of 74.0 Joules/gram when measured by Differential Scanning calorimetry. The test procedures used are ASTM E793-01 and ASTM E794-01 respectively.

104N is a low molecular weight, high density polyethylene wax produced by Hana Corporation. It has a DSC Melt Peak of 118° C., a Melt Enthalpy of 185 Joules/gram, a viscosity of 330 centipoise at 140° C. and a density of 0.93 grams/cc at room temperature.

The 150 MP Paraffin wax is a 66° C. (150° F.) softening point paraffin wax available from a number of suppliers. The melt enthalpy is 187 Joules/gram as measured by DSC. AC-1089 is a polypropylene homopolymer wax sold by Honeywell International Inc. It has a Ring & Ball Softening Point of 146° C., a viscosity of 45 centipoise at 190° C., and a density of 0.91 grams/cc at room temperature.

L-Crysta 7000 is a semi-crystalline polyalphaolefin with a DSC melting point of 75° C. and a melt enthalpy of 131 Joules/gram as measured by DSC. It is manufactured by Idemitsu Kosan Co. of Japan.

Kraton G-1657 is a styrene-ethylene/butylene-styrene block copolymer sold by Kraton Polymers. It has a styrene content of 13%, contains 30% diblock and has a solution viscosity (20% in toluene) of 1200 to 1800 centipoise at 25° C.

The paraffinic process oil is Diana Process Oil PW-90 manufactured by Idemitsu Kosan Co., Ltd. of Japan.

Nyflex 222B is a severely hydrotreated naphthenic process oil available from Nynas Corporation.

Irganox 1010 is a hindered phenol type antioxidant. It is commercially available from Ciba Specialty Chemicals of Tarrytown, N.Y.

Bleed-Through Studies Conducted on Nonwoven Fabric

Several of the prior art mixes shown in Table Two, and all of the inventive mixes from Table Three, were coated on a nonwoven fabric to determine their level of bleed-through at various temperatures. Mixes 1A, 2A and 3A (prior art) as well as mixes A, B, C, D, E and F (inventive) were run to see how these variables effected their ability to resist bleed-through on a standard nonwoven material.

The products were coated using an Acumeter LH-1 coater using a spiral spray adapter to apply the adhesive between a nonwoven fabric and a polyethylene film. The adhesives were applied at an add-on level of 16.3 grams per square meter (gsm) to the nonwoven and after an open time of 0.2 seconds were combined to the polyethylene film using steel to steel nip rollers using a consistent amount of compression. Since various adhesive application temperatures were used, the heated air used to spray the hot melt was also varied and was kept 50° F. higher than the adhesive temperature for any given trial. The nonwoven fabric was a Fibertex 17 gsm SMS (spunbond/meltblown/spunbond) nonwoven. The polyethylene film was a 19 gsm embossed film designated BR 134 and was obtained from Clopay Plastic Products Co. As the adhesive was applied to make the film/nonwoven laminate, the amount of bleed-through was noted along with the degree of adhesive buildup on the steel roller. After the roll of laminate was produced, it was also noted how much blocking and sticking occurred when the roll was unwound. If the adhesive bleeds through the nonwoven, it will stick to the layer of polyethylene adjacent to it in the roll of laminate.

TABLE FOUR (Prior Art)
Bleed-Through Evaluations on Nonwoven Fabric

| Coating Temperature | Product from Table Two (Prior Art) | | |
|---|---|---|---|
| | 1A | 2A | 3A |
| 149° C. | Slight | Moderate | Moderate |
| 163° C. | Slight | Moderate | Moderate |
| 177° C. | Moderate | Severe | Significant |

The levels of bleed-through on the three prior art products (1A, 2A and 3A) from U.S. Pat. No. 6,797,774 would preclude these from ever being run in a commercial setting without significant amounts of downtime and scrap rates.

TABLE FIVE (Inventive)
Bleed-Through Evaluations on Nonwoven Fabric

| Coating Temperature | Product from Table Three | | | | | |
|---|---|---|---|---|---|---|
| | Ex. A | Ex. B | Ex. C | Ex. D | Ex. E | Ex. F |
| 149° C. | None | None | None | None | None | Not run |
| 163° C. | V. Slight | V. Slight | None | None | None | None |
| 177° C. | Slight | V. Slight | V. Slight | None | None | None |

All of the examples in Table Five showed much improved bleed-through resistance on the nonwoven fabric versus the prior art products without the secondary polymer or wax to promote crystallization. Note: "V. Slight" in Table Five means "Very Slight". Thus, not only were the inventive formulations effective to bond the film and nonwoven substrates into a laminate, but they did so without any significant bleed-through of the nonwoven substrate.

The method used to determine density is ASTM D-792-00. The method for determining Melt Index and Melt Flow Rates is ASTM D-1238-04. The molecular weight reported is weight average molecular weight and is determined in accordance with ASTM D-6474-99.

The following Tables Six, Seven and Eight illustrate additional inventive compositions (Examples 1-17) and compare them to three different mixes (Comp. 1, Comp. 2 and Comp. 3). The Comparative examples 1-3 do not contain the low melt point polypropylene homopolymer, or a combination of the low melt point polypropylene homopolymer with another semi-crystalline polymer, and are thus extremely soft as measured by needle penetrometer. Compositions having a needle penetrometer of about 85 dmm or higher, preferably about 90 dmm or higher, are considered too soft.

TABLE SIX

Additional Mixes using Low Melting Point Polypropylene Homopolymers

| Formulation | Comp. 1 | Comp. 2 | Comp. 3 | Ex. 1 | Ex. 2 | Ex. 3 | Ex. 4 |
|---|---|---|---|---|---|---|---|
| Nyflex 222B | 25.0 | 25.0 | 35.0 | 10.0 | 10.0 | 25.0 | 25.0 |
| Piccotac 9095 | | | | | | 49.5 | 14.5 |
| Eastotac H-100R | | 49.5 | 49.5 | 49.5 | | | |
| Sukorez SU-210 | 49.5 | | | | 49.5 | | |
| Escorez 5400 | | | | | | | |
| Paraffin Wax | | | | 10.0 | | 10.0 | |
| 104N | | | | | 10.0 | | 10.0 |
| A-C 1089 | | | | | | | |
| L-Crysta 7000 | | | | | | | |
| Millad NX 8000 | | | | | | | |

TABLE SIX-continued

Additional Mixes using Low Melting Point Polypropylene Homopolymers

| Formulation | Comp. 1 | Comp. 2 | Comp. 3 | Ex. 1 | Ex. 2 | Ex. 3 | Ex. 4 |
|---|---|---|---|---|---|---|---|
| Irganox 1010 | 0.5 | 0.5 | 0.5 | 0.5 | 0.5 | 0.5 | 0.5 |
| Profax RP591V | | | | | | | |
| L-MODU S600 | | | | 30.0 | | 15.0 | 50.0 |
| L-MODU S901 | 25.0 | 25.0 | 15.0 | | 30.0 | | |
| Kraton G1657M | | | | | | | |
| TOTAL | 100.0 | 100.0 | 100.0 | 100.0 | 100.0 | 100.0 | 100.0 |
| Physical Properties | | | | | | | |
| SP - Glycerin (° C.) (or water) | 64 (w) | 66 (w) | 54 (w) | 63 (w) | 108 | 55 (w) | 111 |
| Vis @ 121° C. (cP) | 40900 | 36600 | 1500 | 10520 | 125000 | 900 | 29050 |
| Vis @ 135° C. (cP) | 20850 | 18350 | 820 | 5637 | 61100 | 525 | 16750 |
| Vis @ 149° C. (cP) | 11670 | 10250 | 500 | 3300 | 33300 | 335 | 10270 |
| Vis @ 163° C. (cP) | 7075 | 6250 | 320 | 2085 | 19750 | 225 | 6862 |
| Vis @ 177° C. (cP) | 4550 | 3990 | 215 | 1387 | 12400 | 160 | 4687 |
| Gardner Color (neat) | 2.5 | 2.5 | 2.5 | 3 | opaque | 3 | 2.5 |
| Needle Penetrometer (dmm) | 98 | 95 | 138 | 20 | 3 | 75 | 22 |

TABLE SEVEN

| Formulation | Ex. 5 | Ex. 6 | Ex. 7 | Ex. 8 | Ex. 9 | Ex. 10 | Ex. 11 |
|---|---|---|---|---|---|---|---|
| Nyflex 222B | 25.0 | 10.0 | 20.0 | 20.0 | 31.0 | 10.0 | 11.0 |
| Piccotac 9095 | | | | 37.5 | 12.0 | | |
| Eastotac H-100R | | 25.0 | 37.5 | | | 29.5 | |
| Sukorez SU-210 | 14.5 | 25.0 | | | | | |
| Escorez 5400 | | | | | | | 44.0 |
| Paraffin Wax 104N | 10.0 | 10.0 | 3.5 | 3.5 | | 10.0 | 8.0 |
| A-C 1089 | | | | | 10.0 | | 9.5 |
| L-Crysta 7000 | | | | | | | |
| Millad NX 8000 | | | | | | | |
| Irganox 1010 | 0.5 | 0.5 | 0.5 | 0.5 | 0.5 | 0.5 | 0.5 |
| Profax RP591V | | | | | | | |
| L-MODU S600 | 11.5 | | 38.5 | | 46.5 | 50.0 | |
| L-MODU S901 | 38.5 | 29.5 | | 38.5 | | | 27.0 |
| Kraton G1657M | | | | | | | |
| TOTAL | 100.0 | 100.0 | 100.0 | 100.0 | 100.0 | 100.0 | 100.0 |
| Physical Properties | | | | | | | |
| SP - Glycerin (° C.) (or water) | 77 | 67 (w) | 67 (w) | 69 (w) | 109 | 72 | 105 |
| Vis @ 121° C. (cP) | 93750 | 61100 | 19250 | 96500 | 17450 | 35100 | 47800 |
| Vis @ 135° C. (cP) | 54400 | 31650 | 10570 | 51900 | 10350 | 19750 | 25650 |
| Vis @ 149° C. (cP) | 34150 | 18150 | 6275 | 30500 | 6487 | 12000 | 14820 |
| Vis @ 163° C. (cP) | 22800 | 11120 | 3975 | 19100 | 4330 | 7787 | 9300 |
| Vis @ 177° C. (cP) | 15950 | 7325 | 2665 | 12720 | 3020 | 5337 | 6250 |
| Gardner Color (neat) | 2 | 2.5 | 2.5 | 2.5 | 2.5 | 2.5 | 2.5 |
| Needle Penetrometer (dmm) | 25 | 33 | 24 | 22 | 23 | 27 | |

TABLE EIGHT

| Formulation | Ex 12 | Ex. 13 | Ex. 14 | Ex. 15 | Ex. 16 | Ex. 17 |
|---|---|---|---|---|---|---|
| Nyflex 222B | 16.0 | 27.0 | 16.0 | 27.0 | 27.0 | 27.0 |
| Piccotac 9095 | 22.0 | | | | | |
| EastotacH-100R | | | | | | |
| Sukorez SU-210 | | | | | | |
| Escorez 5400 | 22.0 | 29.0 | 44.0 | 29.0 | 30.0 | 30.0 |
| Paraffin Wax | 8.0 | 6.0 | 8.0 | | 4.0 | 4.0 |
| 104N | 9.0 | | | | | |
| A-C 1089 | | 2.0 | | | | |
| L-Crysta 7000 | | | | 8.0 | | |
| Millad NX 8000 | | | | | | 0.2 |
| Irganox 1010 | 0.5 | 0.5 | 0.5 | 0.5 | 0.5 | 0.5 |
| Profax RP591V | | | 9.0 | | 4.0 | 4.0 |

TABLE EIGHT-continued

| Formulation | Ex 12 | Ex. 13 | Ex. 14 | Ex. 15 | Ex. 16 | Ex. 17 |
|---|---|---|---|---|---|---|
| L-MODU S600 | 22.5 | 24.5 | | 24.5 | 23.5 | 23.3 |
| L-MODU S901 | | 11.0 | 22.5 | 11.0 | 11.0 | 11.0 |
| Kraton G1657M | | | | | | |
| TOTAL | 100.0 | 100.0 | 100.0 | 100.0 | 100.0 | 100.0 |
| Physical Properties | | | | | | |
| SP - Glycerin (° C.) (or water) | 107 | 93 | 127 | 74 | 124 | 146 |
| Vis @ 121° C. (cP) | 16320 | 48000 | | 22800 | | 18100 |
| Vis @ 135° C. (cP) | 9125 | 12100 | 126000 | 12820 | 27800 | 41100 |
| Vis @ 149° C. (cP) | 5487 | 7062 | 25000 | 7850 | 11600 | 11220 |
| Vis @ 163° C. (cP) | 3550 | 4637 | 15720 | 5087 | 7525 | 7287 |
| Vis @ 177° C. (cP) | 2400 | 3150 | 10470 | 3465 | 5200 | 4987 |
| Gardner Color (neat) | | 1 | | 2 | | |
| Needle Penetrometer (dmm) | | 29 | | | 24 | 24 |

What is claimed is:

1. A hot melt adhesive for use on porous substrates, wherein the hot melt adhesive comprises:
    a) about 10% to about 70% by weight of a polypropylene homopolymer having a DSC melting point of less than 100° C.;
    b) about 10% to about 60% of a first tackifying resin having a Ring & Ball Softening Point of about 95° C. to about 140° C.;
    c) about 0% to about 65% of a second tackifying resin that is different than the first tackifying resin;
    d) about 5% to about 50% of a plasticizer;
    e) about 1% to about 40% by weight of a secondary additive that is different than the plasticizer, and said secondary additive having an enthalpy of fusion of greater than 30 Joules/gram;
    f) about 0.1% to about 5% of a stabilizer or antioxidant;
wherein the components total 100% by weight of the composition, and the viscosity of the composition is equal to or less than about 20,000 centipoise (cP) at 163° C. (325° F.).

2. The hot melt adhesive of claim 1 wherein the viscosity of the composition is equal to or less than 15,000 cP at 163° C.

3. The hot melt adhesive of claim 1 wherein the viscosity of the composition is equal to or less than 12,000 cP at 163° C.

4. The hot melt adhesive of claim 1 wherein the polypropylene homopolymer has a DSC melting point of between 60° C. and 90° C.

5. The hot melt adhesive of claim 1 wherein the composition comprises about 15% to about 60% by weight of the polypropylene homopolymer.

6. The hot melt adhesive of claim 1 wherein the composition comprises about 20% to about 50% by weight of the polypropylene homopolymer.

7. The hot melt adhesive of claim 1 wherein the composition comprises about 15% to about 55% by weight of the first tackifying resin.

8. The hot melt adhesive of claim 1 wherein the composition comprises about 20% to about 50% by weight of the first tackifying resin.

9. The hot melt adhesive of claim 1 wherein the first tackifying resin has a Ring and Ball softening point of about 95° C. to about 130° C.

10. The hot melt adhesive of claim 1 wherein the first tackifying resin is selected from the group consisting of (1) natural and modified rosins including gum rosin, wood rosin, tall oil rosin, distilled rosin, hydrogenated rosin, dimerized rosin, and polymerized rosin; (2) glycerol and pentaerythritol esters of natural and modified rosins, including the glycerol ester of pale, wood rosin, the glycerol ester of hydrogenated rosin, the glycerol ester of polymerized rosin, the pentaerythritol ester of hydrogenated rosin, and the phenolic-modified pentaerythritol ester of rosin; (3) copolymers and terpolymers of natural terpenes, such as styrene/terpene and alpha methyl styrene/terpene; (4) polyterpene resins resulting from the polymerization of terepene hydrocarbons, such as the bicyclic monoterpene known as pinene, in the presence of Friedel-Crafts catalysts at moderately low temperatures as well as hydrogenated polyterpene resins; (5) phenolic modified terpene resins and hydrogenated derivatives thereof; (6) aliphatic petroleum hydrocarbon resins resulting from the polymerization of monomers consisting primarily of olefins and diolefins as well as the hydrogenated aliphatic petroleum hydrocarbon resins; (7) cyclic petroleum hydrocarbon resins and the hydrogenated derivatives thereof; and (8) mixtures of two or more of the above described resins.

11. The hot melt adhesive of claim 1 wherein the second tackifying resin is selected from the group consisting of (1) natural and modified rosins including gum rosin, wood rosin, tall oil rosin, distilled rosin, hydrogenated rosin, dimerized rosin, and polymerized rosin; (2) glycerol and pentaerythritol esters of natural and modified rosins, including the glycerol ester of pale, wood rosin, the glycerol ester of hydrogenated rosin, the glycerol ester of polymerized rosin, the pentaerythritol ester of hydrogenated rosin, and the phenolic-modified pentaerythritol ester of rosin; (3) copolymers and terpolymers of natural terpenes, such as styrene/terpene and alpha methyl styrene/terpene; (4) polyterpene resins resulting from the polymerization of terepene hydrocarbons, such as the bicyclic monoterpene known as pinene, in the presence of Friedel-Crafts catalysts at moderately low temperatures as well as hydrogenated polyterpene resins; (5) phenolic modified terpene resins and hydrogenated derivatives thereof; (6) aliphatic petroleum hydrocarbon resins resulting from the polymerization of monomers consisting primarily of olefins and diolefins as well as the hydrogenated aliphatic petroleum hydrocarbon resins; (7) cyclic petroleum hydrocarbon resins and the hydrogenated derivatives thereof; and (8) mixtures of two or more of the above described resins.

12. The hot melt adhesive of claim 1 wherein the composition comprises about 10% to about 45% by weight of the plasticizer.

13. The hot melt adhesive of claim 1 wherein the composition comprises about 15% to about 40% by weight of the plasticizer.

14. The hot melt adhesive of claim 1 wherein the plasticizer is selected from the group consisting of mineral oil and polybutene.

15. The hot melt adhesive of claim 1 wherein the composition comprises about 2% to about 35% by weight of the secondary additive.

16. The hot melt adhesive of claim 1 wherein the composition comprises about 2% to about 30% by weight of the secondary additive.

17. The hot melt adhesive of claim 1 wherein the secondary additive is a semi-crystalline polymer having a heat of fusion of from about 30 Joules/gram to about 80 Joules/gram.

18. The hot melt adhesive of claim 1 wherein the secondary additive is a semi-crystalline polymer having a heat of fusion of from about 40 Joules/gram to about 70 Joules/gram.

19. The hot melt adhesive of claim 1 wherein the secondary additive is a semi-crystalline polymer having a heat of fusion of from about 50 Joules/gram to about 65 Joules/gram.

20. The hot melt adhesive of claim 1 wherein the secondary additive is a semi-crystalline polymer selected from the group consisting of ethylene-vinyl acetate copolymer, polyalphaolefins, and olefin block copolymers.

21. The hot melt adhesive of claim 1 wherein the secondary additive is a wax having a heat of fusion of from about 30 Joules/gram to about 80 Joules/gram.

22. The hot melt adhesive of claim 1 wherein the secondary additive is a wax having a heat of fusion of from about 40 Joules/gram to about 70 Joules/gram.

23. The hot melt adhesive of claim 1 wherein the secondary additive is a wax having a heat of fusion of from about 50 Joules/gram to about 65 Joules/gram.

24. The hot melt adhesive of claim 21 wherein the wax is selected from the group consisting of paraffin wax, microcrystalline wax, and polypropylene wax.

25. The hot melt adhesive of claim 1 wherein the composition further comprises about 0.05% to about 5.0% by weight of a nucleating agent.

26. The hot melt adhesive of claim 25 wherein said nucleating agent is selected from the group consisting of dibenzylidene sorbitol derivatives and aromatic amides.

* * * * *